(12) United States Patent
Ho et al.

(10) Patent No.: US 7,588,942 B2
(45) Date of Patent: Sep. 15, 2009

(54) STANDARD/REFERENCE/CONTROL FOR BLOOD COAGULATION TESTING

(75) Inventors: Timothy Ho, Foothill Ranch, CA (US); James Cole, Yorba Linda, CA (US); Alireza Ebrahim, Laguna Niguel, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 606 days.

(21) Appl. No.: 11/462,436

(22) Filed: Aug. 4, 2006

(65) Prior Publication Data

US 2008/0032405 A1 Feb. 7, 2008

(51) Int. Cl.
*G01N 33/86* (2006.01)
*G01N 33/48* (2006.01)
(52) U.S. Cl. .................. 436/17; 436/8; 436/18; 436/63; 436/66; 436/69; 436/174; 435/2; 435/13; 600/369; 73/64.41; 252/408.1

(58) Field of Classification Search .............. 436/8, 436/17, 18, 63, 66, 69, 174, 175, 176; 435/2, 435/13; 422/73; 600/369; 73/64.41; 252/408.1
See application file for complete search history.

(56) References Cited

U.S. PATENT DOCUMENTS 4,731,330 A * 3/1988 Hill et al. ............. 436/16
5,939,325 A 8/1999 Speck et al.

FOREIGN PATENT DOCUMENTS

WO WO 01/07921 A1 2/2001

* cited by examiner

*Primary Examiner*—Maureen M Wallenhorst
(74) *Attorney, Agent, or Firm*—Townsend and Townsend and Crew LLP.; M. Henry Heines

(57) ABSTRACT

A whole-blood-based substitute composition that is useful in coagulation assays as a standard, reference, control, calibrator, linearity verifier, or training material is prepared by combining a red blood cell lysate that is free of plasma, leukocytes, and platelets with a platelet-free plasma of human origin and an antimicrobial agent.

31 Claims, No Drawings

US 7,588,942 B2

STANDARD/REFERENCE/CONTROL FOR BLOOD COAGULATION TESTING

BACKGROUND OF THE INVENTION

1. Field of the Invention

This invention resides in the field of materials and reagents for tests of human blood.

2. Description of the Prior Art

Tests for determining blood coagulation rates are useful in diagnosing bleeding abnormalities and for monitoring the blood coagulation behavior of a patient that is undergoing treatment or medication for the prevention of blood clot formation. Blood coagulation is caused by the formation of fibrin which results from the action of thrombin on fibrinogen, a soluble component of normal blood, by a succession of reactions that involve a series of blood clotting factors. Thrombin itself is formed from prothrombin by two primary pathways, an extrinsic pathway and an intrinsic pathway, and different coagulation tests measure the viability of one or both of these pathways. The viability of the extrinsic pathway is measured by a determination known in the art as the prothrombin time (PT), while the viability of the intrinsic pathway is measured by a determination known in the art as the activated partial thromboplastin time (APTT). By their own methodologies, both PT and APTT each serve as an indication of the length of time needed for the blood clotting to occur.

Prothrombin time (PT) tests provide an indication of the presence and activity of prothrombin, otherwise known as Factor II, as well as four other clotting factors—Factors I, V, VII, and X. When the level or activity of one or more of these factors is abnormally low, or the activity is blocked by abnormal substances in the subject's blood, the PT value (expressed in seconds) is high. In some cases, this is an indication of a disease condition, while in others the high value is an indication of a successful therapy. Certain medical conditions, for example, are treated by the administration of medications such as heparin and warfarin, that purposely prevent or retard the formation of blood clots. The PT value for a subject undergoing warfarin medication, for example, will be about 1.5 to 2.5 times the result obtained on a healthy subject. The PT value for a healthy subject not under such medication typically falls within the range of about 10 to about 13 seconds.

An activated partial thromboplastin time (APTT) test is commonly performed prior to surgery to confirm that the subject has normal blood clotting behavior. Like PT, APTT is also used to monitor the administration of blood-thinning medications such as heparin, typically by performing the test every two hours and correcting the dosage of the medication until an optimal dosage is reached. For subjects with normal clotting behavior, the APTT value will be within the range of about 25 to about 39 seconds.

A variety of analyzers and reagents are presently available to clinical laboratories for both PT and APTT determinations from commercial suppliers. One such supplier is Diagnostica Stago, Inc. of Parsippany, N.J., USA, whose products include STA-PPT[A]® reagent for APTT tests and STA®-Neoplastine CI Plus reagent for PT tests. The STA-PPT[A]® reagent is used in a test that involves recalcification of plasma in the presence of a standardized amount of cephalin (used as a platelet substitute) and a particulate activator. The STA-Neoplastine CI Plus reagent is used in combination with calcium thromboplastin. An additional supplier is HemoSense, Inc., San Jose, Calif., USA, whose INRatio® Meter is a test device that measures PT and the International Normalized Ratio (INR) which is the ratio of the patient PT to the mean normal PT for a population. The INRatio® Meter obtains these values from one drop of fresh capillary blood from a fingerstick, by use of a recombinant human thromboplastin reagent, and determines the change in impedance of the sample upon the conversion of fibrinogen to fibrin. Another test device is the i-STAT® analyzer sold by i-STAT Corporation of East Windsor, N.J., USA. The i-STAT® analyzer is a hand-held device that contains an artificial thrombin substrate that contains a linkage resembling the site on fibrinogen that thrombin normally cleaves to form a fibrin clot. Thrombin in the blood sample causes cleavage of the substrate and the resulting release of an electroactive compound that is detected amperometrically. The i-STAT analyzer can also be used to measure activated clotting time (ACT), which is the time required for complete activation of the coagulation cascade. ACT determinations are useful for monitoring moderate- and high-level heparin therapy through analysis of arterial and venous blood samples. Complete activation is indicated when extensive or localized clots form as the result of the conversion of fibrinogen to fibrin in the presence of activated thrombin.

Compositions serving as blood sample substitutes are routinely used in conjunction with these various tests, as standards, references, and controls. These compositions are useful in monitoring the precision and accuracy of the instruments or devices, monitoring the condition of any reagents used with the instruments or devices, and comparing patient samples with other samples or with fixed values. Sample substitutes are also used for training purposes when introducing new users to a particular device, instrument, or procedure. A goal in formulating a sample substitute (referred to herein for convenience as a control) is to achieve a composition that is as sensitive as an actual patient sample to all of the analytical variances that are likely to be encountered, and one that reads a value that is within the range of the medical decision point of the assay. The optimal composition is also one that is stable for hours or days after preparation or reconstitution. Other desirable features are low cost, ease of manufacturing, and reproducibility from one lot to the next.

One control that is currently available is the Stago STA-Coag Control (Catalog No. 00679 of Diagnostica Stago), a bi-level lyophilized control that contains citrated normal and abnormal human plasma to represent positive and negative levels, respectively. A tri-level control sold under the name LYPHOCHEK® Coagulation Control is available from Bio-Rad Laboratories, Inc., Hercules, Calif. USA (Catalog Nos. 744, 745, and 746), prepared from processed human plasma and preservatives. Since neither the Stago STA-Coag Control and the LYPHOCHEK® Coagulation Control contain erythrocyte materials, neither of these controls is a whole blood coagulation control. This is a disadvantage since the optimal control material for any whole blood coagulation test, particularly those designed for point-of-care testing, is one that is similar in constitution to the actual sample being tested, and by lacking erythrocytes and erythrocyte components, plasma-based controls lack a major class of components that are present in samples derived from whole blood. Formulations for stable whole blood coagulation controls are disclosed by Speck, R. E., et al. (Analytical Control Systems, Inc.), U.S. Pat. No. 5,939,325, issued Aug. 17, 1999. The Speck controls include non-primate-derived coagulation factors in combination with primate-derived coagulation factors to compensate for any loss of activity over time of the more labile primate-derived factors.

SUMMARY OF THE INVENTION

It has now been discovered that a stable whole-blood-based control for coagulation assays can be prepared by lysing erythrocytes that have been isolated from whole blood and washed to remove platelets, leukocytes, and residual plasma, and combining the lysate with platelet-free buffered plasma of human origin and an antimicrobial agent. If the resulting composition is lyophilized and reconstituted with saline, the reconstituted control will retain its clotting activity for several hours and in many cases several days, in both open-vial and closed-vial storage conditions. The clotting activity of a given control can be adjusted to a desired level by various means, including the use of a plasma that is depleted of coagulation factors or a combination of such a plasma in a selected proportion with a plasma containing coagulation factors at naturally occurring levels, or by varying the proportion of the erythrocyte lysate to the plasma.

DETAILED DESCRIPTION OF THE INVENTION AND PREFERRED EMBODIMENTS

The erythrocytes used in the preparation of the controls in accordance with this invention can be of various origins, such as human, porcine, bovine, equine, avian, caprine, or ovine, but are preferably of primate origin, and most preferably of human origin. The erythrocytes can be harvested from whole blood by conventional methods such as centrifugation, and the harvested erythrocytes can be rendered free of leukocytes, platelets (including platelet membrane components) and residual plasma by washing in an isotonic buffered wash solution. Once separated, the erythrocytes are lysed by conventional lysis techniques. While lysis can be achieved by freezing of the erythrocytes followed by thawing, this procedure is not necessary, and preferred methods are those other than freezing and thawing. Such methods include sonication, osmotic shock, and chemical treatments that dissolve the cell membranes. Osmotic shock is accomplished by suspending the erythrocytes in a hypotonic solution such as deionized water for a sufficient period of time to allow the cell membranes to rupture. Chemical treatments typically consist of exposing the erythrocytes to detergents or surfactants that cause rupture of the membranes. Examples of detergents and surfactants suitable for lysis are NP-40 and other nonylphenol ethoxylates (Dow Chemical Company, Midland, Mich., USA), alkyl aryl polyether alcohols such as TRITON® X-100, BRIJ 58 (polyoxyethylene cetyl ether), CHAPS (a sulfobetaine-type zwitterionic detergent), and sodium dodecyl sulfate. When a detergent or surfactant is used, the appropriate concentration will be readily apparent to those skilled in the art. An appropriate concentration range for NP-40, for example, is from about 0.1% to about 3.0% by weight. Once lysis has occurred, the lysate is cleared of cellular debris and any other solid matter by conventional techniques such as filtration or centrifugation.

In certain embodiments of this invention, the lysate is adjusted to a selected hemoglobin concentration for further control over the composition and behavior of the ultimate control composition. In some cases adjustment will involve a reduction in the hemoglobin concentration and in other cases adjustment will involve an increase in the hemoglobin concentration. A reduction in concentration can be achieved by dilution with buffered saline, and an increase in concentration can be achieved by filtration or dialysis. The target hemoglobin concentration in most cases will range from about 1 g/dL to about 25 g/dL, preferably about 1 g/dL to about 15 g/dL, and most preferably about 10 g/dL to about 15 g/dL.

The plasma used in the practice of this invention is of human origin, and when a coagulation factor-depleted or -deficient plasma is desired, such a plasma can be prepared from normal plasma by conventional techniques. One such technique is ion exchange with a diethylaminoethyl anion exchange resin. Other suitable ion exchange resins will be apparent to those skilled in the art. The degree of depletion of the coagulation factors can be expressed in terms of the PT value of the plasma. Thus, while normal plasmas will have PT values within the range of about 13 to about 18 seconds, a plasma that has a reduced level of coagulation factors may have a PT value of about 200 seconds or greater.

The plasma used in the practice of this invention is platelet-free, and the final composition is devoid of platelet membrane components. The terms "platelet-free" and "devoid" are used herein to include plasmas and compositions that are absolutely devoid of these materials as well as those containing very small amounts of platelet materials, the amounts being so small that the effect of the presence of such materials is no greater than if they were entirely absent. Platelet-free plasma is readily obtained by appropriate filtration, using filtration means known to those skilled in the art. In addition, the erythrocytes prior to lysis can be washed a sufficient number of times to remove platelet materials, and when the erythrocytes are separated from whole blood by centrifuge, the buffy coat can be removed from the packed erythrocytes prior to resuspension and lysis for further assurance of platelet material removal. In the case of erythrocytes, the limitation that the erythrocytes are free of leukocytes, platelets, and residual plasma is intended to be interpreted in the same manner.

The pH of the controls of the present invention is preferably maintained with the range of from about 6.5 to about 7.5 by adding a buffer to the plasma. Conventional buffering agents that can be adjusted to this range can be used. Examples are HEPES (4-(2-hydroxyethyl)-1-piperazineethanesulfonic acid), cacodylate, succinate, MES (2-morpholinoethanesulfonic acid), citrate, maleate, histidine, bis-tris (2-bis(2-hydroxyethyl)amino-2-(hydroxymethyl)-1,3-propanediol), phosphate, ethanolamine, ADA (N-(carbamoylmethyl) iminodiacetic acid), carbonate, ACES (N-(2-acetamido)-2-aminoethanesulfonic acid), PIPES (piperazine-N,N'-bis(ethanesulfonic acid)), MOPSO (3-morpholino-2-hydroxypropanesulfonic acid), imidazole, BES (N,N-bis(2-hydroxyethyl)taurine), MOPS (3-morpholinopanesulfonic acid), TES (N-tris(hydroxymethyl)methyl-2-aminoethanesulfonic acid), MOBS (4-(N-morpholino)butanesulfonic acid), DIPSO (3-[N,N-bis(2-hydroxyethyl)amino]-2-hydroxypropanesulfonic acid), TAPSO (3-[N-tris(hydroxymethyl)methylamino]-2-hydroxypropanesulfonic acid), triethanolamine, pyrophosphate, HEPPSO (N-(2-hydroxyethyl)piperazine-N'-(2-hydroxypropanesulfonic acid)), and POPSO (piperazine-N,N'-bis(2-hydroxypropanesulfonic acid)).

As the antimicrobial component of the compositions of this invention, a variety of conventional antimicrobial agents can be used. Examples are ciprofloxacin, amphotericin B, amikacin, chloramphenicol, sodium azide, and sodium benzoate. The optimal amount of antimicrobial agent will be any amount that has an antimicrobial effect and that does not otherwise interfere with the activity of the components of the composition. In most cases, best results will be achieved with amounts in the range of from about 3 mg/L (mg of antimicrobial agent per liter of total composition) to about 100 mg/L, and preferably from about 10 mg/L to about 50 mg/L. In general, the appropriate amount will vary with the antimicrobial agent and for any particular antimicrobial agent will be readily apparent to those knowledgeable in these agents and their use.

Compositions that produce particular values in the various coagulation tests are achieved by varying the proportion of lysate to plasma, by varying the composition of the plasma, particularly in terms of the levels of the various coagulation factors, or both. The levels of coagulation factors in the plasma can be adjusted to any desired level by combining plasma containing coagulation factors at naturally occurring levels with plasma that is either devoid or depleted of coagulation factors, at the proportions that will produce the desired concentrations. In many cases, it will be useful to prepare a set of two or more compositions to span a range of coagulation rates in a particular coagulation test. When a set of two compositions is prepared, one is preferably within the normal range for a given test and the other within an elevated range representing an abnormally slow coagulation rate. For compositions prepared as controls for a prothrombin time coagulation test, for example, one composition will preferably exhibit a coagulation time within the range of from about 9 seconds to about 18 seconds, and another will preferably exhibit a coagulation time of greater than 24 seconds. For compositions prepared as controls for an activated partial thromboplastin time coagulation test, for example, one composition will preferably exhibit a coagulation time within the range of from about 20 seconds to about 40 seconds, and another will preferably exhibit a coagulation time of greater than 60 seconds. In general, compositions for use as controls for a prothrombin time coagulation test will preferably exhibit a prothrombin time test value of from about 9 seconds to about 100 seconds, and compositions for use as controls for an activated partial thromboplastin time coagulation test will preferably exhibit a prothrombin time test value of from about 25 seconds to about 120 seconds.

For purposes of storage and transportation, the compositions of this invention are conveniently lyophilized, and once ready for use, reconstituted by dissolving in an appropriate reconstitution liquid. In the lyophilized state, the compositions are preferably sealed and maintained in a refrigerated environment. Reconstitution is preferably achieved by dissolving in deionized or distilled water. In certain cases, particularly for point-of care analyzers, for example the i-STAT Analyzer, best results will be obtained when the reconstitution fluid is an aqueous calcium chloride solution. In such a solution, preferred $CaCl_2$ concentrations are those within the range of about 8 mM to about 16 mM.

The following examples are offered for purposes of illustration only.

EXAMPLE 1

A. Preparation of Hemolysate

Human packed red blood cells (RBCs) were obtained by centrifugation of whole human blood for 15 minutes at 3000 RPM at 2-8° C. After centrifugation, the residual plasma was aspirated, together with the anticoagulant that had previously been added to the whole blood, and the buffy coat on the packed cells was removed. The cells were then re-suspended in equal volume of an isotonic saline solution, then centrifuged again for 15 minutes at 3000 RPM at 2-8° C. After centrifugation, the suspension fluid was aspirated, and the cells were re-suspended in isotonic saline solution to a RBC count of 4 to $5 \times 10^6$ RBCs/µL.

The resulting RBC suspension (100 mL) was sonicated using a Branson Sonifier 150 Ultrasonic Cell Disruptor and Homogenizer (Branson Ultrasonics Corporation, Danbury, Conn., USA) at 20 watts for 1 minute. After sonication, the cellular debris was removed by centrifugation at 10,000 RPM for 30 minutes at 2-8° C. The hemolysate was then concentrated to a hemoglobin concentration of 15 g/dL using a dia-filtration apparatus with a molecular weight cut-off of 10,000 Daltons.

B. Preparation of Coagulation Factors-Deficient Plasma

Normal platelet-free human plasma units were thawed in a water bath set at 30-35° C. After thawing, the units were pooled, and 11.9 g/L of HEPES and 30 mg/L of ciprofloxacin were added to the pooled plasma. The resulting combination was mixed for 30 minutes and the pH was adjusted to 6.8. The mixture was then contacted with a diethylaminoethyl anion exchange resin (DEAE Sepharose, Amersham Pharmacia Biotech, Piscataway, N.J., USA) by adding 111 mL of the resin to 1000 mL of the mixture, to deplete the mixture of coagulation factors. Mixing was then continued at 2-8° C. and samples were tested every 15 minutes for PT using a Diagnostica Stago Compact coagulation analyzer until a PT value exceeding 200 seconds was obtained. The suspension of plasma and anion exchange resin was then passed through a 0.8-µm non-glass filter to remove the resin.

C. Preparation of Normal Plasma

Normal platelet-free human plasma units were thawed in a water bath set at 30-35° C. After thawing, the units were pooled, and 11.9 g/L of HEPES and 30 mg/L of ciprofloxacin were added to the pooled plasma. After mixing the additives for 30 minutes, the pH of the pooled plasma was adjusted to 6.8. The resulting mixture was then filtered through a 0.8-µm non-glass filter.

D. Preparation of the Product

Different proportions of filtered hemolysate, factors-deficient plasma, and normal plasma were blended to prepare various compositions with different coagulation times according to both PT and APTT. Each composition was blended and then lyophilized using a freeze-drying cycle consisting of 42 hours with a gradual rise in temperature from −40° C. to 30° C. in 34 hours. The vials were then capped, labeled, and stored at 2-8° C.

The lyophilized compositions were then reconstituted in deionized water, using 1 mL of water for a volume of solids obtained from 1.00 mL of composition prior to lyophilization. A first series of four compositions and their measured values of PT and APTT on a Stago STA Compact Analyzer are listed in Table I below.

TABLE I

Coagulation Rate Values on Stago STA Compact, Expressed as PT and APTT

| Composition No. | Hemolysate (mL) | Factor-Depleted Plasma (mL) | Normal Plasma (mL) | PT (sec) | APTT (sec) | Fibrinogen (mg/dL) |
|---|---|---|---|---|---|---|
| 1 | 100 | 0 | 100 | 14.6 | 78.3 | 248 |
| 2 | 67 | 0 | 100 | 14.2 | 39.8 | 270 |
| 3 | 50 | 80 | 20 | 25.5 | 71.9 | 250 |
| 4 | 34 | 80 | 20 | 26.0 | 63.8 | 268 |

Compositions 1 and 2 were then tested for PT, ACT (activated clotting time), and INR (ratio of PT to mean normal PT) on an i-STAT Analyzer, and the results are listed in Table II below.

TABLE II

Coagulation Rate Values on i-STAT Analyzer
Expressed as PT, ACT and INR

| Composition No. | Hemolysate (mL) | Factor-Depleted Plasma (mL) | Normal Plasma (mL) | PT (sec) | ACT (sec) | INR |
|---|---|---|---|---|---|---|
| 1 | 100 | 0 | 100 | 17.3 | 593 | 1.5 |
| 2 | 67 | 0 | 100 | 16.9 | 492 | 1.4 |

The results shown in Tables I and II indicate that the level of response of the control can be set in a variety of ways for the different test protocols.

E. Stability Test Results

Closed-vial stability tests of the non-reconstituted compositions were performed with an accelerated stability model to predict product shelf life. The procedure consisted of storing vials of product at an elevated temperature (25° C), as opposed to the recommended storage temperature of 2-8° C., for pre-determined periods of time. Samples from the vials were then reconstituted and assayed for PT and APTT to check for decomposition or degradation. The results, when extrapolated to a storage temperature of 2-8° C., indicated that the product would be stable for at least 1 year when stored in closed vials in that temperature range.

Open-vial stabilities were determined by simulating actual use conditions. This was done by placing vials containing Compositions 1 and 2 in reconstituted form in a refrigerator at 2-8° C., removing the vials from the refrigerator every 8 hours, allowing the vials to equilibrate at room temperature for 15 minutes, and opening the vials and exposing their contents to the laboratory environment for 15 minutes before sampling the vial contents, re-closing the vials and returning the vials to the refrigerator. Samples from the vials were assayed for PT and APTT on a Stago STA Compact Analyzer, and the results are listed Tables III and IV, respectively. The results indicate that the product will be stable for at least 8 hours when reconstituted, opened, and stored at 2-8° C.

TABLE III

Open-Vial Stability Test Results on Stago STA Compact,
Expressed as PT at 2-8° C.

| | PT (seconds) | |
|---|---|---|
| Time (hours) | Composition No. 1 | Composition No. 2 |
| 0 | 12.7 | 23.8 |
| 8 | 12.8 | 23.9 |
| 24 | 13.0 | 24.7 |

TABLE IV

Open-Vial Stability Test Results on Stago STA Compact,
Expressed as APTT at 2-8° C.

| | APTT (seconds) | |
|---|---|---|
| Time (hours) | Composition No. 1 | Composition No. 2 |
| 0 | 30.3 | 62.6 |
| 8 | 32.3 | 66.7 |
| 24 | 32.8 | 68.7 |

Tables III and IV demonstrate that both compositions are stable in reconstituted form at normal use conditions for over 24 hours.

The foregoing descriptions are offered primarily for purposes of illustration. Further variations and modifications, although not mentioned herein but nevertheless apparent to those skilled in the art, that utilize the basic concepts of this invention are still within the scope thereof, as expressed in the appended claims.

What is claimed is:

1. A composition of known coagulation behavior that is substantially non-varying with time, for use in conjunction with blood coagulation rate determinations, said composition comprising:
   a red blood cell lysate obtained by lysing red blood cells that are free of plasma, leukocytes, and platelets and platelet membrane components;
   platelet-free plasma of human origin buffered at a pH of from about 6.5 to about 7.5, said platelet-free plasma that is either (i) plasma depleted of coagulation factors, (ii) plasma with coagulation factors at naturally occurring levels, or (iii) a combination of (i) and (ii); and
   an antimicrobial agent;
   said composition being devoid of platelet membrane components.

2. The composition of claim 1 wherein said red blood cells are of primate origin.

3. The composition of claim 1 wherein said red blood cells are of human origin.

4. The composition of claim 1 wherein said red blood cell lysate has a hemoglobin concentration of from about 1 g/dL to about 25 g/dL.

5. The composition of claim 1 wherein said red blood cell lysate has a hemoglobin concentration of from about 1 g/dL to about 15 g/dL.

6. The composition of claim 1 wherein said red blood cell lysate has a hemoglobin concentration of from about 10 g/dL to about 15 g/dL.

7. A set of first and second compositions, each in accordance with claim 1, wherein said red blood cell lysate and said platelet-free plasma are at selected lysate:plasma proportions, said lysate:plasma proportion of said first composition differing from said lysate:plasma proportion of said second composition such that said first composition exhibits a coagulation time ranging from about 9 to about 18 seconds and said second composition exhibits a coagulation time of about 24 seconds or greater, by a prothrombin time coagulation test.

8. A set of first and second compositions, each in accordance with claim 1, wherein said platelet-free plasma consists of a selected proportion of plasma depleted of coagulation factors to plasma with coagulation factors at naturally occurring levels, said proportion of said first composition differing from said proportion of said second composition such that said first composition exhibits a coagulation time ranging from about 9 to about 18 seconds and said second composition exhibits a coagulation time of about 24 seconds or greater, by a prothrombin time coagulation test.

9. A set of first and second compositions, each in accordance with claim 1, wherein said red blood cell lysate and said platelet-free plasma are at selected lysate:plasma proportions, said lysate:plasma proportion of said first composition differing from said lysate:plasma proportion of said second composition such that said first composition exhibits a coagulation time ranging from about 25 to about 40 seconds and said second composition exhibits a coagulation time of about 60 seconds or greater, by an activated partial thromboplastin time coagulation test.

10. A set of first and second compositions, each in accordance with claim 1, wherein said platelet-free plasma consists of a selected proportion of plasma depleted of coagulation factors to plasma with coagulation factors at naturally occurring levels, said proportion of said first composition differing from said proportion of said second composition such that said first composition exhibits a coagulation time ranging from about 25 to about 40 seconds and said second composition exhibits a coagulation time of about 60 seconds or greater, by an activated partial thromboplastin time coagulation test.

11. A process for the manufacture of a composition of known coagulation behavior that is substantially non-varying with time, for use in conjunction with blood coagulation rate determinations, said process comprising:
(A) lysing red blood cells that are free of plasma, leukocytes, and platelets and platelet membrane components to form a lysate;
(B) combining said lysate with
(a) platelet-free plasma of human origin buffered at a pH of from about 6.5 to about 7.5, said platelet-free plasma that is either (i) plasma depleted of coagulation factors, (ii) plasma with coagulation factors at naturally occurring levels, or (iii) a combination of (i) and (ii), and
(b) an antimicrobial agent.

12. The process of claim 11 wherein said lysing of (A) is performed by a method other than freezing and thawing of said red blood cells.

13. The process of claim 11 wherein said lysing of (A) is performed by sonication.

14. The process of claim 11 wherein said lysing of (A) is performed by osmotic shock.

15. The process of claim 11 wherein said lysing of (A) is performed by treatment of said red blood cells with a chemical lysing agent.

16. The process of claim 11 wherein said red blood cells are of primate origin.

17. The process of claim 11 wherein said red blood cells are of human origin.

18. The process of claim 11 further comprising lyophilizing the product of step (B).

19. The process of claim 11 further comprising (A') treating said lysate to achieve a modified a hemoglobin concentration therein prior to step (B) by diluting said lysate with saline.

20. The process of claim 11 further comprising (A') treating said lysate to achieve a modified a hemoglobin concentration therein prior to step (B) by concentrating said lysate.

21. The process of claim 11 wherein said lysate prior to step (B) has a hemoglobin concentration of from about 1 g/dL to about 25 g/dL.

22. The process of claim 11 wherein said lysate prior to step (B) has a hemoglobin concentration of from about 1 g/dL to about 15 g/dL.

23. The process of claim 11 wherein said lysate prior to step (B) has a hemoglobin concentration of from about 10 g/dL to about 15 g/dL.

24. A process for the manufacture of first and second compositions of known coagulation behavior that is substantially non-varying with time in conjunction with blood coagulation rate determinations, said process comprising forming first and second compositions by the process of claim 11, wherein step (B) comprises combining said lysate with said platelet-free plasma of human origin at a selected lysate:plasma proportion, and said first and second compositions differ in said selected lysate:plasma proportion such that said first composition exhibits a coagulation time ranging from about 9 to about 18 seconds and said second composition exhibits a coagulation time of about 24 seconds or greater, by a prothrombin time coagulation test.

25. A process for the manufacture of first and second compositions of known coagulation behavior that is substantially non-varying with time for use in conjunction with blood coagulation rate determinations, said process comprising forming first and second compositions by the process of claim 11, wherein said platelet-free plasma of human origin of step (B) consists of a selected proportion of plasma depleted of coagulation factors to plasma with coagulation factors at naturally occurring levels, and said first and second compositions differ in said selected proportion such that said first composition exhibits a coagulation time ranging from about 9 to about 18 seconds and said second composition exhibits a coagulation time of about 24 seconds or greater, by a prothrombin time coagulation test.

26. A process for the manufacture of first and second compositions of known coagulation behavior that is substantially non-varying with time for use in conjunction with blood coagulation rate determinations, said process comprising forming first and second compositions by the process of claim 11, wherein step (B) comprises combining said lysate with said platelet-free plasma of human origin at a selected lysate:plasma proportion, and said first and second compositions differ in said selected lysate:plasma proportion such that said first composition exhibits a coagulation time ranging from about 25 to about 40 seconds and said second composition exhibits a coagulation time of about 60 seconds or greater, by an activated partial thromboplastin time coagulation test.

27. A process for the manufacture of first and second compositions of known coagulation behavior that is substantially non-varying with time for use in conjunction with blood coagulation rate determinations, said process comprising forming first and second compositions by the process of claim 11, wherein said platelet-free plasma of human origin of step (B) consists of a selected proportion of plasma depleted of coagulation factors to plasma with coagulation factors at naturally occurring levels, and said first and second compositions differ in said selected proportion such that said first composition exhibits a coagulation time ranging from about 25 to about 40 seconds and said second composition exhibits a coagulation time of about 60 seconds or greater, by an activated partial thromboplastin time coagulation test.

28. A process for the manufacture of a plurality of compositions of known coagulation behavior that is substantially non-varying with time for use in conjunction with blood coagulation rate determinations, said process comprising forming a plurality of compositions by the process of claim 11, wherein step (B) comprises combining said lysate with said platelet-free plasma of human origin at a selected lysate:plasma proportion, and said plurality of compositions differ in said selected lysate:plasma proportion such that one of said compositions exhibits a coagulation time within a range of from about 9 to about 18 seconds and others of said compositions exhibit coagulation times outside of said range, by prothrombin time coagulation test.

29. A process for the manufacture of a plurality of compositions of known coagulation behavior that is substantially non-varying with time for use in conjunction with blood coagulation rate determinations, said process comprising forming a plurality of compositions by the process of claim 11, wherein step (B) comprises combining said lysate with said platelet-free plasma of human origin at a selected lysate:plasma proportion, and said plurality of compositions differ in said selected lysate:plasma proportion such that one of said compositions exhibits a coagulation time within a range of from about 25 to about 40 seconds and others of said compositions exhibit coagulation times outside of said range, by an activated partial thromboplastin time coagulation test.

30. A process for the manufacture of a plurality of compositions of known coagulation behavior that is substantially non-varying with time for use in conjunction with blood coagulation rate determinations, said process comprising forming a plurality of compositions by the process of claim 11, wherein said platelet-free plasma of human origin of step (B) consists of a selected proportion of plasma depleted of coagulation factors to plasma with coagulation factors at naturally occurring levels, and said plurality of compositions differ in said selected proportion of plasma depleted of coagulation factors to plasma with coagulation factors at naturally occurring levels, such that one of said compositions exhibits a coagulation time within a range of from about 9 to about 18 seconds and others of said compositions exhibit coagulation times outside of said range, by prothrombin time coagulation test.

31. A process for the manufacture of a plurality of compositions of known coagulation behavior that is substantially non-varying with time for use in conjunction with blood coagulation rate determinations, said process comprising forming a plurality of compositions by the process of claim 11, wherein said platelet-free plasma of human origin of step (B) consists of a selected proportion of plasma depleted of coagulation factors to plasma with coagulation factors at naturally occurring levels, and said plurality of compositions differ in said selected proportion of plasma depleted of coagulation factors to plasma with coagulation factors at naturally occurring levels, such that one of said compositions exhibits a coagulation time within a range of from about 25 to about 40 seconds and others of said compositions exhibit coagulation times outside of said range, by an activated partial thromboplastin time coagulation test.

* * * * *